United States Patent [19]

Kiedik et al.

[11] Patent Number: 5,502,016
[45] Date of Patent: Mar. 26, 1996

[54] METHOD TO TREAT AN ION-EXCHANGER CATALYST FOR THE PROCESS OF BISPHENOL-A SYNTHESIS

[75] Inventors: Maciej Kiedik; Andrzej Krueger; Józef Kołt; Antoni Korek; Wojciech Balcerowiak; Jacek Hetper; Maria Majchrzak, all of Kedzierzyn-Koźle; Jan Niedziela, Kobylice; Ryszard Kościuk, Kędzierzyn-Koźle; Anna Rzodeczko, Kędzierzyn-Koźle; Jerzy Mróz, Kędzierzyn-Koźle; Zbigniew Swiderski, Kędzierzyn-Koźle, all of Poland

[73] Assignees: Instytut Ciezkiej Syntezy Organicznej Blachownia; Zaklady Chemiczne Blachownia, both of Kedzierzyn-Kozle, Poland

[21] Appl. No.: 248,317

[22] Filed: May 23, 1994

[30] Foreign Application Priority Data

Jun. 22, 1993 [PL] Poland .................................. 299459

[51] Int. Cl.⁶ .................................................. B01S 37/30
[52] U.S. Cl. ........................... 502/11; 502/12; 502/159; 568/728
[58] Field of Search .................. 502/11, 12, 159; 521/36, 33; 568/716, 728

[56] References Cited

U.S. PATENT DOCUMENTS 4,820,740  4/1989  Li ............................... 502/159 X

*Primary Examiner*—Michael Lusignan
*Attorney, Agent, or Firm*—Bauer & Schaffer

[57] ABSTRACT

In the process of bisphenol-A systhesis a method for controlling the water content of the resultant cation-exchanger bed wherein an acid ion-exchanger resin in the form of a sulphonated styrene-divinylbenzene copolymer is washed with phenol and the resulted washing is contacted with a basic ion-exchanger resin. Water is removed from the washing by distillation, and the dewatered phenol is recycled to wash the cation-exchanger bed. The catalyst bed is then washed with a mixture of phenol acetone and water, and this washing is contacted with the basic ion-exchange resin and recycled to wash the cation exchanger bed so as to obtain the desired moisture content.

1 Claim, No Drawings

METHOD TO TREAT AN ION-EXCHANGER CATALYST FOR THE PROCESS OF BISPHENOL-A SYNTHESIS

The subject of this invention is a method to treat an ion-exchanger catalyst in the form of an acid ion-exchanger resin, used for the process of bisphenol-A (2,2-di)4-hydroxyphenyl(propane) synthesis.

The phenol-acetone condensation reaction to form bisphenol-A and water is effected in the presence of acid ion-exchanger resins (cation exchangers). The cation exchangers for use in the bisphenol-A manufacturing process are either commercial products or species modified with promotors, increasing the catalytic activity and selectivity of ion-exchangers. In most cases, treatment of ion-exchange catalysts refers to supporting them on promotors. The promotors may also be used as a component of the reaction mixture.

Also well known is a method to purify the ion-exchanger resins for use in the production of bisphenol-A in order to diminish the product loss and improve its coloration which are both affected by the presence of low-molecular sulfonic acids being released from cation exchangers such as a sulphonated styrene-divinylbenzene copolymer.

According to Patent EP 0324080, the treatment of an ion-exchanger catalyst consists in contacting the cation exchanger, first with a base such as a 1–20% aqueous solution of sodium hydroxide, then with a strong acid such as a 2–10% aqueous solution of sulphuric acid, 3–5 milliequivalents of the strong acid being used per each one milliequivalent of the sulphonic acid to be neutralized. Between these operations, as well as upon completion of the treatment, the cation exchanger is washed with water. A disadvantage of that method to treat ion-exchanger catalysts is formation of large amounts of liquid waste containing inorganic salts. Other known methods to stabilize the product coloration consist in using, in the process to obtain bisphenol-A, basic ion-exchanger resins with which the various bisphenol-A-containing process streams are contacted prior to the final product recovery. A drawback of such solutions is that the resulting product is obtained with deteriorated quality if amines are released by the anion-exchanger.

The object of this invention was to develop a method to treat an ion-exchange catalyst for the process of bisphenol-A synthesis, enabling reduction of sulphur content in the resulted product, without constantly having to use the anion-exchanger in the process to manufacture bisphenol-A. Increased sulphur concentrations in the product are known to have an adverse effect on its color stability.

Unexpectedly, the wet cation exchanger treated by contacting it, at a certain temperature, with phenol and a liquid mixture of a specified composition, which are then contacted with the anion exchanger and recycled to the cation exchanger treatment process, was found to permit the product to be obtained with a positively lower sulphur content when used as a catalyst in the bisphenol-A synthesis process.

The gist of the invention is that the wet cation exchanger, being a basic ion-exchange resin in the form of a sulphonated styrene-divinylbenzene copolymer, is washed with phenol having a water content of 0.01–2% by weight, at a temperature of 50°–90° C. The resulted washings containing 40–99.5% by weight of phenol and 0.5–60% by weight of water are then contacted with the basic ion-exchanger resin whereupon water is removed from the washings by distillation and the dewatered phenol is recycled in order to wash the cation-exchanger bed, to finally obtain a water content of not more than 15% by weight of the cation exchanger. The cation-exchanger bed is then washed at a temperature of 60°–100° C. with a mixture containing 35–80% by weight of phenol, 0.5–5% by weight of acetone, 5–30% by weight of bisphenol-A, 0.5–30% by weight of by-products of the phenol-acetone condensation reaction and 0.1–3% by weight of water, and the washings are contacted with the basic ion-exchange resin and recycled in order to wash the cation exchanger. Treatment of the ion-exchanger catalyst is continued to obtain a moisture content in the cation exchanger of not more than 5% by weight.

Following treatment by the method of the invention, when used in the bisphenol-A synthesis process the cation exchanger permits the product to be obtained with its sulphur content several times as small, while eliminating any free amines, since the anion exchanger is used in the process to treat the ion exchanger, rather than in the process to manufacture bisphenol-A.

EXAMPLES 1–7

200 ml of the sulphonic cation exchanger in the hydrogen form, with a predetermined moisture content was placed in a glass column (25 mm in diameter) equipped with a heating jacket and directly connected to another glass column (15 mm in diameter), also having a heating jacket and packed with 50 ml of Amberlyst A-21, an anion exchanger in the form of a weakly basic ion-exchanger resin with functional groups in the form of a tertiary amine. Treatment of the cation exchanger was effected by directing, to the column $K_1$, a liquid stream which, at a controlled flowrate and temperature, $T_{K1}$, was flowing downward, first through the cation-exchanger bed in the Column $K_1$, then through the anion-exchanger bed in the Column $K_2$ at temperature $T_{K2}$. Liquid phenol containing 0.1% and 0.2% by weight of water was used initially for washing the cation-exchanger bed; the washings were dewatered by distillation prior to being recycled to the cation-exchanger treatment process. A liquid mixture containing phenol, acetone, bisphenol-A, by-products of the acetone-phenol condensation reaction and a small amount of water was then circulated through the columns $K_1$ and $K_2$ (Examples 2–7). In the Comparative Example, phenol alone was used for treating the cation exchanger. The moisture content of the cation exchanger was determined at intervals during the treatment.

The treated cation exchanger was used as the catalyst of bisphenol-A synthesis. A 500-ml glass flask equipped with a thermometer, reflux condenser and magnetic stirrer was filled with 70 ml of the treated cation exchanger and 400 ml of a mixture containing phenol and acetone in a molar ratio of 7:1, whereafter bisphenol-A synthesis was conducted at 80° C. for 5 hrs. The phenol-bisphenol A adduct was recovered by crystallization straight from the postreaction mixture and decomposed in a simple vacuum distillation unit while distilling off the separated phenol, at a vacuum of 50 mm Hg. The crude bisphenol-A obtained was analyzed to determine its sulphur content. The treated species of cation exchangers, the treatment process parameters, the content of moisture in the cation exchanger and sulphur in the crude bisphenol-A are shown in Table 1. Compositions of the streams used for treating the cation exchangers are given in Table 2.

TABLE 1

| Example number | Cation exchanger Name | Cation exchanger DVB percentage | N° of stream used for treatment of cation exchanger with composition acc. to Table 2 | Rate of liquid flow through Columns $K_1$ and $K_2$ [dm³/hr] | Bed temperature in Columns [°C.] $T_{K1}$ | Bed temperature in Columns [°C.] $T_{K2}$ | Moisture content in cation-exchanger [% by weight] before treatment with liquid stream | Moisture content in cation-exchanger [% by weight] after treatment with liquid stream | Sulpher content in crude bisphenol-A [ppm] |
|---|---|---|---|---|---|---|---|---|---|
| 1 (comparative) | Amberlyst-31 | 4 | 1 | 0.2 | 60 | 50 | 63.1 | 4.5 | 5.1 |
| 2 | Amberlyst-31 | 4 | 1 | 0.2 | 50 | 50 | 63.1 | 13.6 | 0.3 |
|   |   |   | 4 | 0.2 | 70 | 60 | 13.6 | 4.1 |   |
| 3 | Amberlyst-32 | 2 | 2 | 0.3 | 80 | 70 | 82.2 | 14.9 | 0.6 |
|   |   |   | 5 | 0.3 | 60 | 70 | 14.9 | 4.8 |   |
| 4 | Wofatit FK-8 | 8 | 1 | 0.4 | 60 | 60 | 54.3 | 12.8 | 0.5 |
|   |   |   | 4 | 0.4 | 80 | 80 | 12.8 | 3.9 |   |
| 5 | Amberlyst-15 | 20 | 2 | 0.1 | 70 | 60 | 52.1 | 13.4 | 0.7 |
|   |   |   | 3 | 0.1 | 70 | 50 | 13.4 | 2.6 |   |
| 6 | Amberlyst-36 | 12 | 1 | 0.5 | 90 | 90 | 58.0 | 14.3 | 0.8 |
|   |   |   | 3 | 0.5 | 100 | 100 | 14.3 | 2.8 |   |
| 7 | Amberlyst XN1010 | 50 | 1 | 0.2 | 60 | 50 | 22.7 | 10.6 | 0.5 |
|   |   |   | 6 | 0.2 | 70 | 60 | 10.6 | 1.9 |   |

TABLE 2

| N° of stream used for treating cation-exchanger under conditions of Table 1 | Stream composition, percentage by weight | | | | |
|---|---|---|---|---|---|
|  | Phenol | Acetone | Bisphenol-A | By-products total | Water |
| 1 | 99.9 | — | — | — | 0.1 |
| 2 | 98.0 | — | — | — | 2.0 |
| 3 | 77.5 | 0.8 | 7.6 | 13.3 | 0.8 |
| 4 | 54.6 | 2.8 | 18.5 | 22.7 | 1.4 |
| 5 | 36.6 | 3.5 | 28.7 | 28.4 | 2.8 |
| 6 | 80.5 | 4.8 | 13.7 | 0.8 | 0.2 |

We claim:

1. A method for the treatment of an ion exchange catalyst for the process of bisphenol-A synthesis, wherein the catalyst forms an acid ion exchange bed of a sulphonated styrene-divinylbenzene copolymer containing 2–50% divinylbenzene, in hydrogen form, and having a moisture content of up to 85% by weight, comprising the steps or sequence of:

(1) passing phenol containing 0.01–2% by weight water through the cation exchange bed at a temperature in the range 50°–90° C. to provide a resultant first effluent containing 40–99.5% by weight phenol and 0.5–60% by weight water, (2) running said resultant first effluent through a basic anion exchange resin to obtain a resultant second effluent, (3) removing water from the second effluent by distillation to obtain a dewatered phenol, (4) recycling said dewatered phenol through the cation exchange bed and its resultant first effluent throughout anion exchange resin until the water content of said cation exchanger is at or below 15%, (5) washing the catalyst bed at a temperature of 60°–100° C. with a mixture consisting of 35–80% by weight phenol, 0.5–5% by weight of acetone, 5–30% by weight of bisphenol-A, 0.5–30% by weight of the phenol-acetone condensation reaction by-products and 0.1–3% by weight of water, (6) contacting the effluent with the basic ion exchange resin, (7) recycling said contacted effluent through said cation exchange bed and basic ion exchange resin until the cation exchanger has a moisture content of not more than 5% by weight.

* * * * *